(12) United States Patent
Schön et al.

(10) Patent No.: US 10,067,059 B2
(45) Date of Patent: Sep. 4, 2018

(54) DEVICE FOR SIMULTANEOUS FLUORESCENCE CONTRASTING EFFECT IN TRANSMITTED LIGHT AND REFLECTED LIGHT

(71) Applicant: Carl Zeiss Microscopy GmbH, Jena (DE)

(72) Inventors: Peter Schön, Göttingen (DE); Cornelia Bendlin, Göttingen (DE)

(73) Assignee: Carl Zeiss Microscopy GMBH, Jena (DE)

(*) Notice: Subject to any disclaimer, the term of this patent is extended or adjusted under 35 U.S.C. 154(b) by 142 days.

(21) Appl. No.: 15/354,673

(22) Filed: Nov. 17, 2016

(65) Prior Publication Data

US 2017/0138855 A1 May 18, 2017

(30) Foreign Application Priority Data

Nov. 18, 2015 (DE) .................. 10 2015 222 768

(51) Int. Cl.
| | |
|---|---|
| H01J 40/14 | (2006.01) |
| G01N 21/64 | (2006.01) |
| G02B 21/16 | (2006.01) |
| G02B 21/24 | (2006.01) |
| G02B 5/00 | (2006.01) |

(52) U.S. Cl.
CPC ........... G01N 21/645 (2013.01); G02B 5/005 (2013.01); G02B 21/16 (2013.01); G02B 21/241 (2013.01); *G01N 2021/6471* (2013.01); *G01N 2201/062* (2013.01)

(58) Field of Classification Search
CPC ...... G02B 21/04; G02B 21/006; G02B 21/16; G02B 21/241
USPC .......................... 250/234–236; 359/368, 386
See application file for complete search history.

(56) References Cited

U.S. PATENT DOCUMENTS

| | | | |
|---|---|---|---|
| 6,867,915 B2 * | 3/2005 | Mueller ............... | G02B 21/088 359/368 |
| 6,917,468 B2 * | 7/2005 | Thomas ............. | G02B 21/0032 359/368 |
| 2013/0256563 A1 * | 10/2013 | Kalkbrenner ...... | G01N 21/6428 250/459.1 |

* cited by examiner

*Primary Examiner* — Kevin Pyo
(74) *Attorney, Agent, or Firm* — Nixon Peabody LLP; Jeffrey L. Costellia

(57) ABSTRACT

The invention relates to a device for simultaneous fluorescence contrasting effect in transmitted light and reflected light, having a reflected light optical path for focusing of the excitation light via a lens onto a sample, having a fluorescence signal, which extends from the sample and is directed onto the same lens, having a dichroite, an emission filter, and a detection unit for the purpose of separating the excitation light from the fluorescence signal and for detection, having a luminescent layer behind the sample and a diaphragm for partial coverage of the excitation optical path between the sample and the luminescent layer, whereby a part of the excitation optical path, which impinges onto the luminescent layer, emits light, which irradiates the sample past the diaphragm by forming an oblique transmitted light illumination.

11 Claims, 4 Drawing Sheets

DEVICE FOR SIMULTANEOUS FLUORESCENCE CONTRASTING EFFECT IN TRANSMITTED LIGHT AND REFLECTED LIGHT

TECHNICAL FIELD

The invention relates to a device for simultaneous fluorescence contrasting effect in transmitted light and reflected light, having a reflected light optical path for focusing of the excitation light via a lens onto a sample.

BACKGROUND

Microscopy has an important part in life sciences. Biological samples can be present on a number of different sample carriers, for example between slide and cover glass, in Petri dishes or microtiter plates. They can be still alive or fixed, non-dyed or dyed. In general, they can be observed in transmitted light and reflected light.

In case of transmitted light illumination, the light emitted by a light source irradiates the sample and is collected by the lens and directed onto a detector. Part of the light is absorbed by the sample, diffused or refracted, which manifests as a contrast in intensity on the detector. If the sample does not absorb any or hardly any light, which is often the case for thin biological specimens, particularly if they are non-dyed, the phase structure of the sample can be made visible by means of a number of contrast methods (phase contrast, differential interference contrast—DIC, etc.). Admittedly, all these methods have in common that they can represent the shape of biological samples, such as cells, for example, as well as some of their components (cell nucleus, et al.); functional statements, however, are frequently impossible.

Fluorescence dyes, however, allow dyeing of specifically targeted cell components. The dyes are excited with light of suitable wavelength for the purpose of imaging, which is ordinarily implemented by reflected light illumination, with the illumination light being focused through the lens onto the observed sample area.

The fluorescence signal—red-shiftet with respect to the excitation light—is acquired by the same lens, separated from the excitation light by means of a dichroite and matching filters, and directed to the camera or the oculars. Statements regarding the functions and functional changes in the cells can be derived from the fluorescence images. In doing so, however, information on the cell shape in its entirety is often missing.

It is therefore advantageous to combine transmitted light and fluorescence images with one another because the corresponding images supplement each other regarding their statements. Therefore typically are required two illumination systems, which are separated from one another and which are being operated sequentially. Thus, a transmitted light image of a sample can be acquired, first, for example, and subsequently a fluorescence image is acquired.

To save time, transmitted light and fluorescence images can also be implemented in parallel. Therefore are required two cameras on the one hand. On the other hand, the wavelength of the transmitted light must be a different one than that of the fluorescence signal so that both signals can be separated from one another by means of a dichroic mirror. Therefore, the time gain is bought with a significantly more complex structure.

It would be advantageous to combine the transmitted light and fluorescence images with one another without having to accept time loss or significantly more complex structures.

U.S. Pat. No. 4,515,445 for example, discloses a method, in which a reflected light illumination is directed onto the sample. That part of the light, which is transmitted through the sample, is reflected back through a mirror in a plane conjugate to the sample plane and, in doing so, functions as transmitted light during the second round of sampling. This results in an image, which is created both by parts of transmitted light and by light, which is reflected by the sample. This method, however, is not suitable for fluorescence images, because, admittedly, a dichroic mirror can be introduced into the optical path, which separates the light emitted by the fluorophores from the excitation light, but would also filter out the transmitted light during the second round of sampling. The advantage of such method would only consist in directing the light, which was not utilized to excite the fluorophores during the first round of sampling, to the sample, once again, thereby increasing the excitation intensity. The result, however, is a standard fluorescence image.

A different solution is described in Ding et al., Optics Express 20, 14100-14108 (2012). The sample is illuminated point for point in a laser scanning configuration, albeit obliquely, in each case. A fluorescent layer is located behind the sample, which layer is excited by the laser light, which is passing the sample, and in turn sends out a fluorescence signal. This signal, in turn, serves as transmitted light, if it is caught by the lens through the sample and directed in the direction of the detector. As a result of the excitation light being incident obliquely to the sample, it also excites a region behind the sample in the fluorophore layer, which is positioned offset with respect to the optical axis. Therefore, the transmitted light sent out from there, also passes the scanned sample point at just that angle. This results in an image, which is similar to that of a classical oblique illumination. If the sample itself is fluorescent, as well, the fluorescence signal of the sample is added to the image. Such structure, however, is extremely sophisticated and expensive.

BRIEF DESCRIPTION

Proceeding from the disadvantages of the solutions of the prior art, the invention is based on the object of further developing a device for simultaneous fluorescence contrasting effect in transmitted light and reflected light to the effect that apparatus complexity is reduced and the solution is also employable for wide-field systems.

This object is solved by means of a device according to the invention of the type described in the beginning with the features of claim 1. Advantageous embodiments are stated in the dependent claims 2 to 11.

A first embodiment is provided with a conventional reflected light optical path, with the excitation light being focused onto the sample through the lens and the fluorescence signal of the sample being caught by the same lens, being separated from the excitation light by means of a dichroite and an emission filter, and being detected by a detection unit, advantageously by a camera.

Advantageously, an excitation filter can be located in the reflected light optical path, which filter controls the wave length range of the excitation light. The device is also provided with a luminescent layer in a suitable distance behind the sample, which permits a sufficiently strong signal, which is caused by the luminescent layer. Additionally, a diaphragm is positioned between sample and luminescent layer, which diaphragm, however, does not completely cover the optical path in the direction of the luminescent layer. The excitation light, which passes the sample, is then mostly blocked by this diaphragm, a small part, however, does reach the luminescent layer laterally. The excited parts of the luminescent layer emit luminescent light, which in turn reaches the sample laterally past the diaphragm. This occurs at a certain angle, so that this light acts similar to an oblique transmitted light illumination. Because it is a matter of luminescent light, it can pass the dichroite and the emission filter and reach the camera.

The acquired camera image has similarities to the contrast of an oblique illumination as well as fluorescence signals of the sample itself. If the sample does not fluoresce, only the impression of an oblique illumination remains.

To be able to adjust the optimum contrast impression, the diaphragm is arranged adjustably in an advantageous embodiment (for example pivotable around a suitable axis, displaceable, or both), so that it blocks a more or less large percentage of the illumination light. In doing so, the angle range, at which the illumination light impinges onto the luminescent layer, as well as the angle range, at which the luminescent light passes the sample as transmitted light, can be adjusted. This adjustment is particularly dependent on the numerical aperture (NA) of the lens. NA specifies the maximum beam angle with respect to the optical axis, which can be caught by the lens. The larger the numerical aperture, the larger is the critical angle. Dependent thereon, the diaphragm can cover the luminescent layer in such way that larger angles of incidence can be utilized. In doing so, the adjustment of the diaphragm can be implemented manually or by motor.

A broad-banded luminescent layer proves to be advantageous, because it can be used for different excitation wavelengths. If the device, however, is to be mainly used for non-luminescent samples, a layer can be used, which can only be excited by a narrow wavelength range, and a suitable illumination wave length can be selected. The same applies if the samples only fluoresce in a narrowly limited wavelength range.

If a second image is acquired, with the diaphragm covering the luminescent layer to the extent that no reflected light reaches it any longer, this image exclusively contains the fluorescence percentage of the sample itself. Furthermore, this image can be subtracted from the image with a partially opened diaphragm to obtain a transmitted light image with oblique illumination percentages.

A second embodiment of the invention is suitable for microscopes with reflected light and transmitted light optical path and can be completely managed without any additional elements in the optical path.

Light sources for transmitted light illuminations are increasingly white light LEDs. They consist of a LED, which emits in blue or UV spectral range, as well as a luminescent layer, which emits broad-banded. The resulting light is a mixture of the LED excitation wavelength and the luminescence of the layer. A similar structure is used in the second embodiment of the device according to the invention. If the sample is excited by means of reflected light, a major part of the light passes the sample and passes through the entire transmitted light optical path in reverse direction until it impinges onto the luminescent layer of the white light LED. There, it excites the luminescent layer, which in turn sends out light, which passes the sample as transmitted light, once again, and is directed to the camera. This path is commonly blocked by a diaphragm in the transmitted light optical path, because the reflexes of the different interfaces in the transmitted light optical path and the luminescence of the white light LED are sources of interference, which are suppressed as far as possible. If this diaphragm, however, is not completely shut, a part of the reflected light can pass the transmitted light optical path and excite the luminescent layer of the white light LED. The resulting light thereof passes through the transmitted light optical path in the usual way and a small part of the light reaches the sample passing the not completely closed diaphragm more or less comparable to an oblique illumination, and finally delivers a correspondingly contrasted transmitted light image to the camera.

Analogously to the first embodiment, the contrast impression can be optimized here, as well, by closing the diaphragm—depending on the numerical aperture of the lens and the sample—varying in width. Likewise, considerations regarding separation of the transmitted light contrast and the sample fluorescence signals maintain their validity. Of course, an image with an entirely closed diaphragm can be acquired as well, which only contains the fluorescence percentage of the sample itself.

One possibility of controlled selection of transmitted light with a specific range of the numerical aperture subject to the condition of conventional oblique illumination consists of employing a correspondingly variable diaphragm in the plane of the aperture diaphragm (or a plane conjugate thereto) of the transmitted light optical path. This variation, however, would have the disadvantage with respect to the diaphragm position below the object plane, that undesired reflexes and possibly even intrinsic florescence, caused by the optical components irradiated between the object plane and the diaphragm for oblique illumination, could not be suppressed in the light path.

This poses the question why the white light LED is not utilized in the usual way as transmitted light source, as opposed to using the detour of exciting its luminescent layer by means of reflected light illumination.

Of course, the direct path is possible, as well. The diaphragm of the transmitted light optical path could be partially closed in the described manner to achieve a type of oblique illumination.

The utilization of reflected light illumination, in contrast, has an advantage. The fluorescence signal of the sample is typically many orders of magnitude smaller than the intensity of the excitation light. As a result of the same excitation light being used for both the sample itself and the luminescent layer of the white light LED, the resulting signals thereof are also in the same order of magnitude. This facilitates simultaneous acquisition of both signals or, in the alternative—in one case when the diaphragm is completely closed and in one case when it uncovers limited access to the transmitted light optical path—quick acquisition of two images, one of which only with the fluorescence percentage of the sample itself, and one with both fluorescence percentages, without any further elements having to be connected into the optical path.

If the white light LED itself were to act as light source for the transmitted light, it would deliver a significantly higher intensity than the florescence of the sample, and either an additional absorption filter would have to be introduced into the transmitted light optical path or the period of exposure of the camera would have to be adjusted separately.

Furthermore, the strength of the absorption filter would have to be adjusted separately to any wave length of the reflected light illumination, as well. This entire complexity is obsolete by means of the device according to the invention, because the reflected light illumination itself excites the luminescent layer of the white light LED.

The only apparatus interference, which is required to utilize such standard microscope with transmitted light and reflected light optical path in terms of the device according to the invention, consists of modifying the diaphragm in the transmitted light optical path in such way that it can laterally open the transmitted light optical path, yet also block it increasingly up to complete coverage.

A further advantageous embodiment consists of using a variable, pivotable diaphragm at a suitable location, to be able to obtain an optical path in the style of an oblique illumination or similar to that from the transmitted light optical path, having a variably sized light beam from different directions to, in turn, obtain the best possible image impression depending on the structure of the specimen. For example, the pivotable diaphragm could be designed in such way that it is situated in an insertion, on the one hand, in which it can be pivoted around its center and, on the other hand, in which it can be moved within the plane, in which it is arranged in x and y directions from the center, which corresponds to the optical axis. In doing so, the outer part of the diaphragm has to be designed in a way that it uncovers a different amount of surface in the direction of the luminescent layer on one side—depending on the displacement from the center. The light path can also be completely covered by displacement of the diaphragm.

In a different advantageous embodiment, the entire diaphragm could be pivoted eccentrically around an axis, which does not correspond to the optical axis. By means of correspondingly adjusted diaphragm contours and suitable positioning of the diaphragm in the optical path it can therefore also be achieved that a light beam can reach the specimen in the style of an oblique illumination or averted thereof from different directions (though not symmetrically to the optical axis). The light path to the luminescent layer can be interrupted completely by means of a corresponding diaphragm shape in this embodiment, as well.

BRIEF DESCRIPTION OF THE DRAWINGS

The device according to the invention will be explained in detail below by reference to embodiment examples. The drawings show in.

Figure 1:
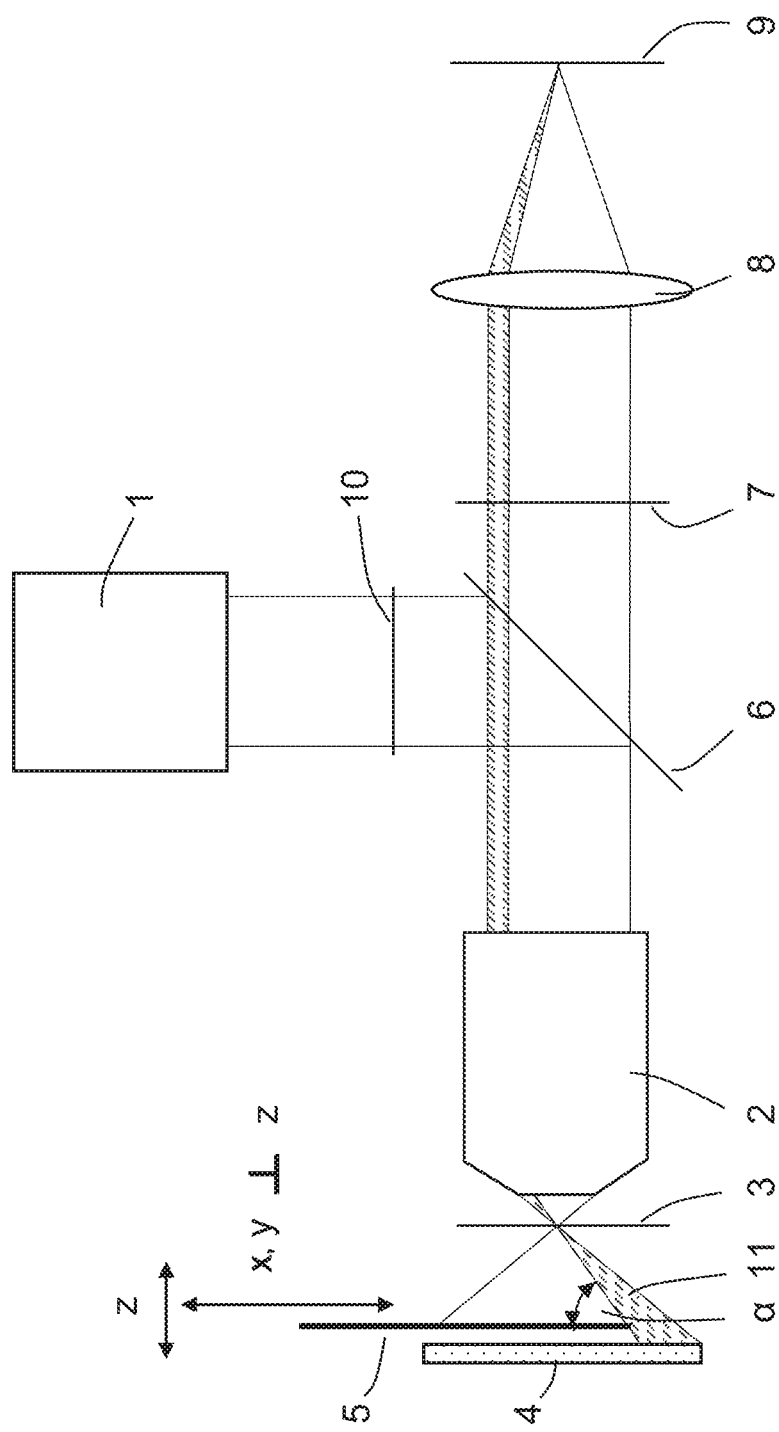
FIG. 1: a schematic illustration of the device according to the invention having a luminescent layer.

The present disclosure is susceptible of various modifications and alternative forms, and some representative embodiments have been shown by way of example in the drawings and will be described in detail herein. It should be understood, however, that the inventive aspects are not limited to the particular forms illustrated in the drawings. Rather, the disclosure is to cover all modifications, equivalents, and alternatives falling within the spirit and scope of the disclosure as defined by the appended claims.

DETAILED DESCRIPTION OF ILLUSTRATED EXAMPLES

FIG. 1 shows the device according to the invention, having a reflected light optical path commonly known in the art for focusing of the excitation light, which extends from an illumination source 1 and reaches the sample plane 3 via a lens 2. A broad-banded luminescent layer is located behind the sample plane 3, for example a fluorescent layer 4. For purposes of partial coverage of the excitation light, which impinges onto the luminescent layer 4 through the sample plane 3, a displaceable diaphragm 5 is located between the sample plane 3 and the luminescent layer 4, which can be pivoted around a suitable axis and/or in x and y directions, i.e., in the plane perpendicular to the pivot axis, which diaphragm can be additionally designed to be displaceable in z direction, as well, i.e., displaceable in parallel to the pivot axis.

The fluorescence signal of a sample arranged in the sample plane 3 is acquired by the same lens 2, separated from the excitation light by means of a dichroite 6 and an emission filter 7, and detected by a detection unit arranged as camera 9 via a tube lens 8.

An excitation filter 10 is located in the reflected light optical path, which filter controls the wavelength range of the excitation light.

The excitation light, which passes the sample, is largely blocked by the diaphragm 5, whereas a small part impinges onto the luminescent layer 4 laterally past the diaphragm 5. The excited parts of the luminescent layer 4 emit the luminescent light, which, in turn, reaches the sample laterally by the diaphragm 5. This occurs under a schematically implied angle α depending on the design of the diaphragm 5 and the numerical aperture of the lens used, so that the light 11 has an effect similar to an oblique transmitted light illumination.

The angle range at which the illumination light impinges onto the luminescent layer 4, as well as the angle range at which the luminescent light passes the sample as transmitted light can be conditioned by the adjustable diaphragm 5.

Since it is a matter of luminescent light, it can pass the dichroite 6 as well as the emission filter 7 at least partially, and reach camera 9.

The acquired camera image has similarities to the contrast of an oblique illumination as well as fluorescence signals of the sample itself. If the sample itself does not fluoresce, this leaves the impression of an oblique illumination.

Figure 2:
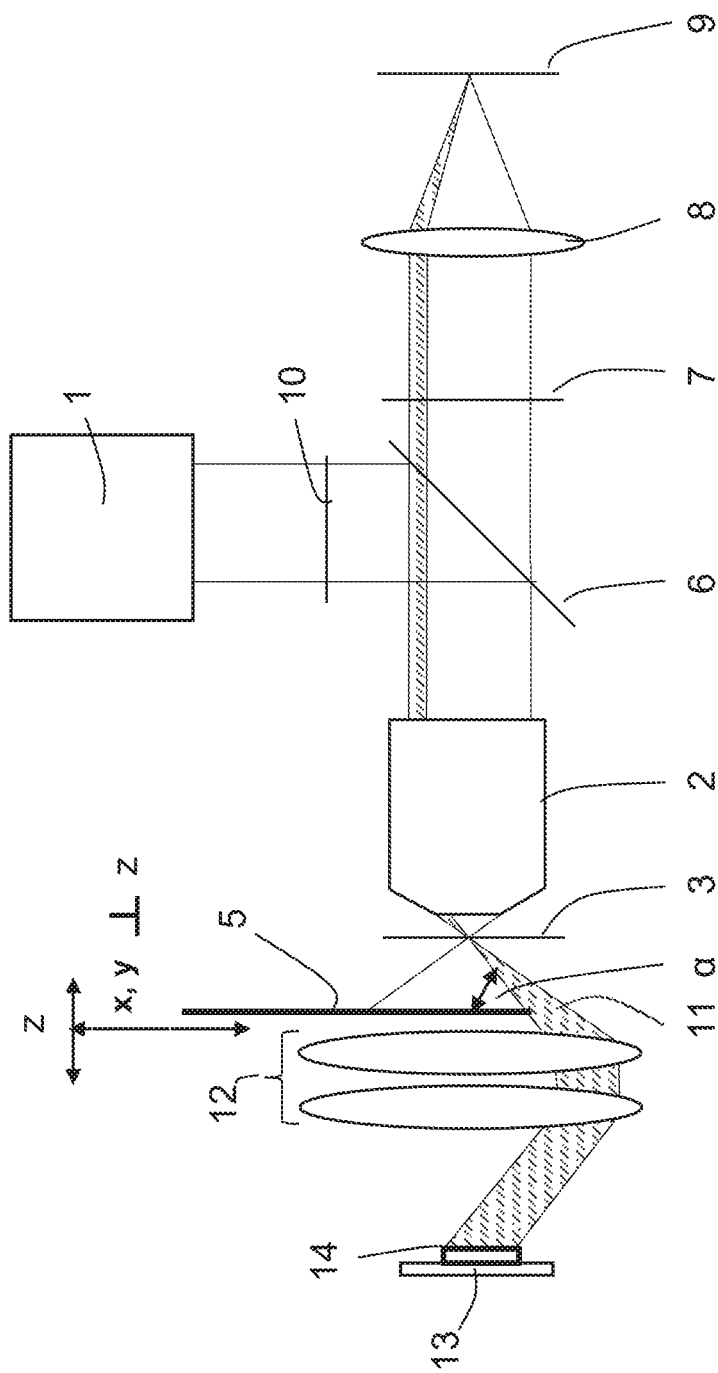
FIG. 2: a schematic illustration of the device according to the invention having a luminescent layer as component of a transmitted light illumination.

The embodiment represented in FIG. 2 is suitable for microscopes with reflected light and transmitted light irradiation and manages entirely without any additional elements in the optical path. It shows the device according to the invention having a reflected light optical path analogous to FIG. 1.

In difference to the embodiment according to FIG. 1, a transmitted light illumination optics 12, consisting for example of a collector and a condenser, is positioned behind the adjustable diaphragm 5 in viewing direction from the sample plane 3.

A white light LED 13 is utilized as light source for the transmitted light illumination optics, which LED emits in the blue and in UV spectral range, and which has a luminescent layer 14. In doing so, the resulting light is a mixture of the excitation wavelength of the white light LED 13 and the luminescence of layer 14.

If the sample is excited by means of the reflected light optical path, a large part of the light impinging onto the sample plane passes the sample and passes through the entire transmitted light optical path in the opposite direction, until it impinges onto the luminescent layer 14 of the white light LED 13. There, it excites the luminescent layer 14, which, in turn, sends out light, which subsequently passes the sample as transmitted light, again, and is directed to the camera 9. This path is conventionally blocked by a diaphragm 5 in the transmitted light optical path, because the reflexes of the various interfaces in the transmitted light optical path as well as the luminescence of the white light LED 13 are sources of interference, which are suppressed as far as possible.

If diaphragm 5 is not completely closed, part of the reflected light can pass the transmitted light optical path to excite the luminescent layer 14 of the white light LED 13. The resulting light thereof subsequently passes the transmitted light optical path, whereby a small part of the light 11 reaches the sample by the not completely closed diaphragm 5. This is more or less comparable to an oblique illumination and provides a contrasted transmitted light image on camera 9, analogous to the first embodiment.

Similar to the first embodiment, the contrast impression can be optimized, here, as well, by closing diaphragm 5—depending on the numerical aperture of lens 2 and the sample—with varying width. Likewise, the considerations regarding the separation of the transmitted light contrast and the sample fluorescence signals maintain their validity. Of course, an image with completely closed diaphragm 5 can be acquired, as well, which only contains the fluorescence percentage of the sample itself.

Figure 3:
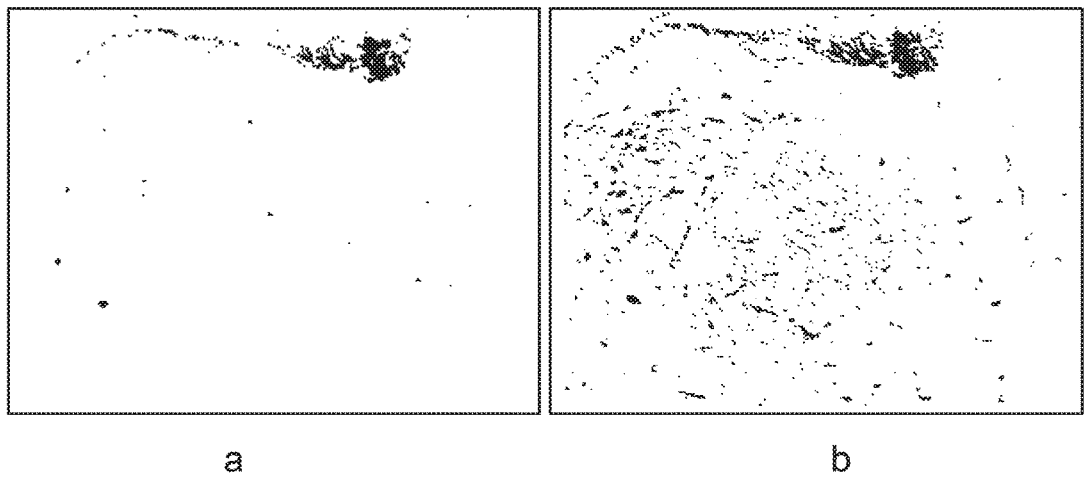
FIG. 3: the schematic illustration of a brain slice acquired with the device of FIG. 2, FIG. 4: a schematic illustration of the intensity profile.

FIG. 3 shows the representation of a brain slice, originally acquired as a conventional grey-level image according to the second embodiment, in an inverted, purely black-white contrast, in which black image components characterize the respective brightest signals in the original image, whereby the image with closed diaphragm 5 was acquired in drawing a, whereas diaphragm 5 was partially open in drawing b.

Drawing b depicts significantly finer details compared to the pure fluorescence image according to drawing a.

If only a grey-level image is present, which was acquired with a partially opened diaphragm 5, further additional information can be gathered thereof. In such image, the information from the transmitted light illumination overlay the luminescent layer and the sample fluorescence. Both signals, however, can be separated to a limited extent. The strength of the transmitted light contrast essentially depends on the absorption properties of the sample as well as its phase gradient. Particularly non-dyed samples absorb only a very low percentage of the light. The transmitted light contrast is then created by the phase gradient of the sample and turns out the stronger, the stronger this gradient is at each sample point. Depending on which algebraic sign it has, the corresponding part of the image appears brighter or darker than the average value. Fluorescent structures in the sample, however, can emit very strong signals. A possibility for separation of both percentages is to determine a range of intensity to determine the mean intensity of the image, which comprises the contrast to be expected based on the transmitted light illumination. All points, which are depicted brighter than this range, then originate from fluorescent locations of the sample itself and therefore can be represented separately. Lightly fluorescent sample structures, however, are not acquired, in doing so.

Figure 4:
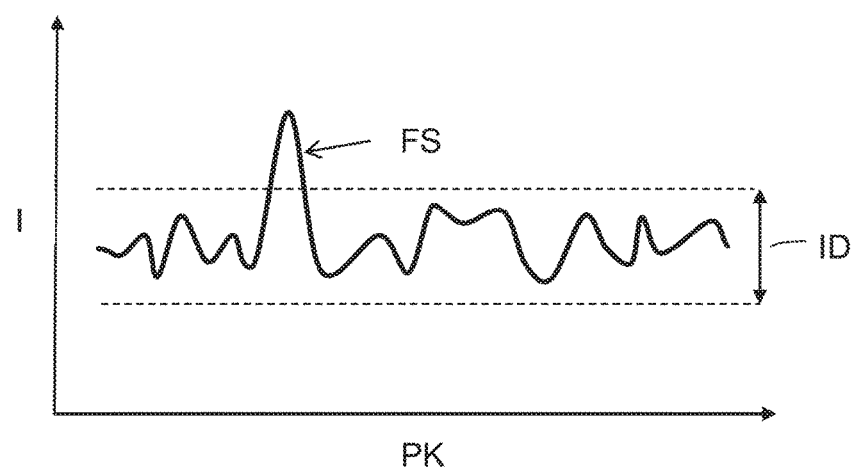

FIG. 4 illustrates this embodiment by means of a profile of the intensity I depending on the profile coordinate PK, having the illustration of the intensity range of the transmitted light image ID and the fluorescence peak FS.

Figure 5:
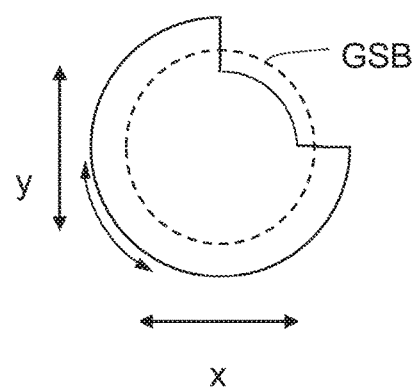
FIG. 5: a schematic illustration of the diaphragm.

FIG. 5 shows a schematic illustration of the diaphragm 5, having the adjustment possibilities with respect to the displacement in x and y directions as well as rotation around a pivot axis. Further, the outer limit of the beam GSB can be seen, here. The use of the variable, pivotable diaphragm 5 effects achievement of an optical path in the style of an oblique illumination or similar thereto from the transmitted light optical path, having a variably sized light beam from different directions, to in turn achieve the best possible image impression depending on the structure of the sample.

The pivotable diaphragm 5 could, for example, be designed in such way that it is situated in an application in which it can be rotated around its center, on the one hand, and, on the other hand, in which it can be moved in x and y directions from the center, which corresponds to the optical axis, within the plane, in which it is arranged. In doing so, the outer part of the diaphragm 5 has to be designed in a way that it uncovers a different amount of surface in the direction of the luminescent layer 14 on one side—depending on the displacement from the center. By means of displacement of diaphragm 5 in x and y directions, the light path to the luminescent layer 14 can also be covered in its entirety.

The diaphragm 5 could be excentric pivoted around an axis, which does not correspond to the optical axis. By means of correspondingly adjusted diaphragm contours and suitable positioning of the diaphragm 5 in the optical path, it can therefore also be achieved that a light beam can reach the specimen in the style of an oblique illumination or averted thereof from different directions (though not symmetrically to the optical axis). The light path to the luminescent layer 14 can be interrupted completely by means of a corresponding diaphragm shape in this embodiment, as well.

Figure 6:
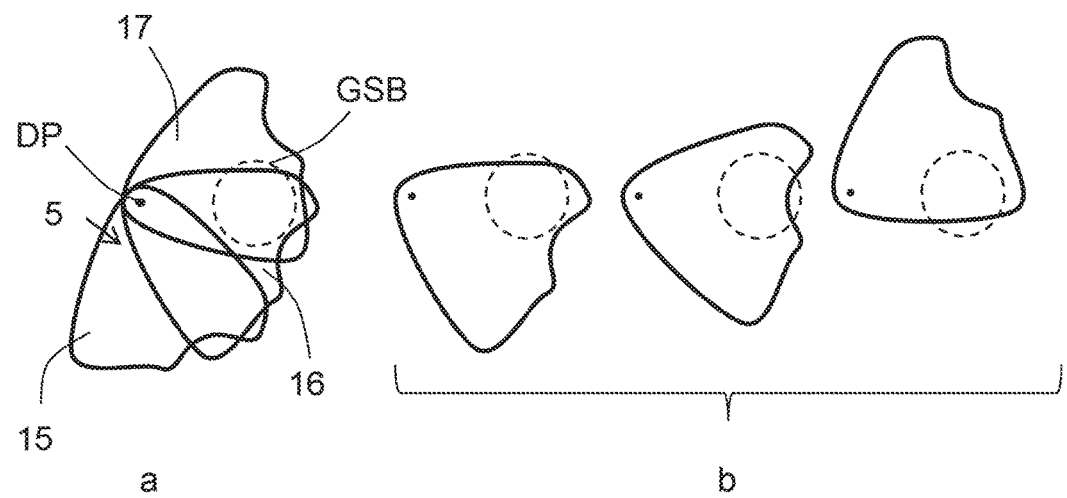
FIG. 6: schematic illustrations of the coverage of the beam.

FIG. 6 shows schematic illustrations of the coverage of the beam with diaphragm 5. DP is illustrated as the pivot point of the diaphragm 5, GSB as the outer limit of the beam, and 15, 16 and 17 as three different positions of diaphragm 5 in drawing a, having illustrations of:

15: beam uncovered for transmitted light images,
16: beam partially covered for combined florescence and transmitted light images, and
17: beam completely covered for fluorescence images.

in drawing b can be seen variable, partial coverage of the beam by diaphragm 5 to control the angle of incidence of the beam.

This application is based on German Patent Application no. 102015222768.5 filed with the German Patent Office on Nov. 18, 2015, the entire contents of which are hereby incorporated by reference.

The invention claimed is:

1. A device for simultaneous fluorescence contrasting effect in transmitted light and reflected light, comprising
   a reflected light optical path for focusing the excitation light via a lens to a sample,
   a fluorescence signal, which extends from the sample and is directed to the same lens,
   a dichroite, an emission filter, and a detection unit, for the purpose of separating the excitation light from the fluorescence signal and for detection
   having a luminescent layer behind the sample and
   a diaphragm for partial coverage an excitation optical path between the sample and the luminescent layer, whereby light is emitted by means of that part of the excitation optical path, which impinges onto the luminescent layer, which light irradiates through the sample by the diaphragm by forming an oblique transmitted light illumination.

2. The device according to claim 1, characterized in that the luminescent layer is a layer of a lighting source of a transmitted light illumination optics.

3. The device according to claim 1, characterized in that the detection unit is a camera.

4. The device according to claim 1, characterized in that an excitation filter is arranged in the reflected light optical path for the purpose of control of the wavelength range of the excitation light.

5. The device according to claim 1, characterized in that the luminescent layer is designed broad-banded.

6. The device according to claim 1, characterized in that the luminescent layer is arranged behind the sample with a distance of a few mm.

7. The device according to claim 2, characterized in that the luminescent layer is the luminescent layer of a white light LED.

8. The device according to claim 1, characterized in that the diaphragm is arranged pivotable around an axis and/or moveable in x and y directions from the center, which corresponds to the optical axis.

9. The device according to claim 1, characterized in that the diaphragm is eccentrically pivotable around an axis, which axis does not correspond to the optical axis.

10. The device according to claim 8, characterized in that the focusing of the diaphragm can be realized manually or by motor.

11. The device according to claim 8, characterized in that the diaphragm can be varied with respect to light transmittance.

* * * * *